US00PP24055P3

(12) United States Plant Patent

Zaiger et al.

(10) Patent No.: US PP24,055 P3

(45) Date of Patent: Dec. 3, 2013

(54) INTERSPECIFIC TREE NAMED 'EBONY ROSE'

(50) Latin Name: ***Interspecific Prunus* species**
Varietal Denomination: Ebony Rose

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 64 days.

(21) Appl. No.: 13/506,343

(22) Filed: Apr. 13, 2012

(65) Prior Publication Data

US 2013/0276177 P1 Oct. 17, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth habit.
2. Regular and productive bearer of medium to large fruit.
3. Fruit with attractive dark red skin and flesh color.
4. Fruit with an average Brix of 17.2° and a good balance between acid and sugar.
5. Fruit with very good flavor and eating quality.
6. Fruit with good handling and shipping qualities.

1 Drawing Sheet

Botanical designation: Interspecific *Prunus* species.
Variety denomination: 'Ebony Rose'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of interspecifics and plum trees, which are known to us, and mentioned herein, 'Flavorich' Interspecific (U.S. Plant Pat. No. 8,546), 'Crimson Kat' Interspecific (U.S. Plant Pat. No. 22,740), 'Dapple Dandy' Interspecific (U.S. Plant Pat. No. 9,254) the proprietary plum seedling '95LD384' (non-patented) and the proprietary interspecific seedling '168LM497' (non-patented).

STATEMENT REGARDING FEDERALLY SPONSORED RESEARCH AND DEVELOPMENT

Not applicable.

Origin of the Variety

The new and distinct interspecific tree consists of the combination of *Prunus salicina, Prunus armeniaca* and *Prunus persica*. It was originated by us in our experimental orchard located near Modesto, Calif. as a first generation cross between 'Crimson Kat' Interspecific (U.S. Plant Pat. No. 22,740) and our proprietary interspecific seedling '168LM497' (non-patented). The pollen parent '168LM497' (non-patented) originated from a cross of our proprietary plum seedling '95LD384' (non-patented) and 'Flavorich' Interspecific (U.S. Plant Pat. No. 8,546). A large number of these first generation crosses were grown and budded on to older 'Nemaguard' Rootstocks (non-patented) to accelerate tree and fruit development. Under close and careful observation, one such seedling exhibited desirable tree and fruit characteristics and was selected in 2009 for additional asexual propagations and commercialization.

Asexual Reproduction of the Variety

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree which consists of [(Plum×Plumcot)×(Plum×Peach-cot)×Plum], which is of large size, vigorous, upright growth and a productive and regular bearer of medium to large size, clingstone fruit with very good flavor and eating quality. The fruit is further characterized by having dark red skin and flesh with good handling and storage quality. In comparison to its seed parent 'Crimson Kat' Interspecific (U.S. Plant Pat. No. 22,740) the fruit of the new variety has darker red flesh and is approximately 65 days earlier in maturity. In comparison to its pollen parent '168LM497' (non-patented) the fruit of the new variety has solid dark red skin instead of mottled red skin, more delicate flavor and is approximately 60 days earlier in maturity. In comparison to the commercial interspecific 'Dapple Dandy' (U.S. Plant Pat. No. 9,524) the fruit of the new variety has solid dark red skin instead of mottled red skin, darker red flesh and is approximately 10 days earlier in maturity.

PHOTOGRAPH OF THE VARIETY

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 4 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 4 year old specimens grown near Modesto, Calif., with color in accordance with Munsell Book of Color.

Tree:

*Size.*—Large, pruned to 3 to 3.5 meters in height and width for economical harvesting of fruit.

*Vigor.*—Vigorous, growth of 1.5 to 2 meters the first growing season, varies with type of soil, fertility and cultural practices.

*Form.*—Upright, usually pruned to vase shape.

*Branching habit.*—Upright, crotch angle approximately 30°, increases with heavy crop load.

*Productivity.*—Productive. Sets 1.5 to several times the amount of fruit desired, thinning and spacing of fruit, necessary for marketable size fruit. Varies with climatic conditions during bloom time.

*Bearer.*—Regular. Good fruit set 3 consecutive years. No alternate bearing observed.

*Fertility.*—Self-sterile, pollinator required.

*Density.*—Medium dense. Usually pruned to vase shape to increase amount of sunlight to center of tree to enhance fruit color, Brix and health of fruit wood.

*Hardiness.*—Tree grown in USDA Hardiness Zone 9. Winter chilling requirement approximately 600 hours at or below 45° F. Hardy in all stone fruit growing areas of California.

Trunk:

*Size.*—Large. Average circumference 50.8 cm at 18 cm above ground on a 4 year old tree.

*Stocky.*—Medium stocky.

*Texture.*—Medium shaggy, increases with age of tree.

*Color.*—Varies from 2.5Y 7/2 to 2.5Y 5/2.

Branches:

*Size.*—Medium. Average circumference 8.5 cm when measured at a height of 1.0 meters above ground. Crotch angle approximately 30°, increases with heavy crop load.

*Surface texture.*—New growth relatively smooth. Mature growth moderately rough, roughness increases with age.

*Lenticels.*—Average number 64 in a 25.8 sq cm section. Average length 1.9 mm. Average width 1.1 mm. Color varies from 7.5YR 6/8 to 7.5YR 5/10.

*Color.*—New growth varies from 5GY 6/8 to 7.5R 4/6 where exposed to the sun. Mature growth varies from 7.5YR 4/2 to 10YR 2/2, varies with age of growth.

Leaves:

*Size.*—Small to medium. Average length 77.1 mm. Average width 32.7 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentation over midrib and pinnate venation, glabrous. Lower surface relatively smooth except for small ridges created by midrib and pinnate venation, glabrous.

*Petiole.*—Average length 12.0 mm. Average width 1.1 mm. Longitudinally grooved. Surface — glabrous. Color varies from 5GY 6/6 to 2.5YR 3/6.

*Glands.*—Globose. Size — very small. Average length 0.4 mm. Average diameter 0.3 mm. Number varies from 2 to 4, average number 3. Located primarily on the upper portion of the petiole and the base of the leaf blade. Color varies from. 2.5YR 5/4 to 2.5YR 5/6.

*Stipules.*—Average number 2. Average length 7.4 mm. Edges — pectinate. Color varies from 5GY 6/8 to 5GY 7/8.

*Color.*—Upper surface varies from 5GY 3/6 to 7.5GY 3/4. Lower surface varies from 7.5GY 4/4 to 5GY 4/4. Midvein color varies from 10Y 7/4 to 7.5Y 7/4.

Flower buds:

*Size.*—Small to medium. Average length 9.4 mm. Average diameter 4.2 mm.

*Hardiness.*—Hardy with respect to California winters.

*Form.*—Plump, conical, becomes more elongated as bud matures.

*Pedicel.*—Average length 6.8 mm. Average width 0.5 mm. Color varies from 2.5GY 8/6 to 2.5GY 7/8.

*Color.*—N 9.5/ (white).

*Number of buds per spur.*—Varies from 3 to 7, average number 5.

Flowers:

*Blooming period.*—Date of First Bloom Feb. 13, 2011. Date of Petal Fall Feb. 23, 2011, varies slightly with climatic conditions.

*Size.*—Medium. Average height 10.8 mm. Average diameter 22.3 mm.

*Petals.*—Normally 5, alternately arranged to sepals. Size — medium. Average length 10.8 mm. Average width 7.3 mm. Form — elliptical. Margin — sinuate. Both upper and lower surface glabrous. Color N 9.5/ (white).

*Sepals.*—Normally 5, alternately arranged to the petals. Size — small. Average length 2.4 mm. Average width 2.2 mm. Shape — triangular. Margin — entire. Both upper and lower surface glabrous: Color — upper surface varies from 2.5GY 6/6 to 5GY 6/6. Lower surface varies from 2.5GY 6/6 to 5GY 6/8.

*Stamens.*—Average number per flower 27. Average filament length 7.2 mm. Filament color N 9.5/ (white). Anther color varies from 2.5Y 7/10 to 5Y 8/8.

*Pollen.*—Present, self-sterile, pollinator required. Color varies from 2.5Y 7/10 to 5Y 7/12.

*Pistil.*—Normally 1. Average length 8.2 mm. Position of stigma even with anthers. Surface — glabrous: Color varies from 10Y 8/6 to 10Y 7/6.

*Fragrance.*—Slight fragrance.

*Color.*—N 9.5/ (white).

*Number flowers per flower bud.*—Average 2, varies from 1 to 3.

*Pedicel.*—Average length 8.6 mm. Average width 0.5 mm. Color varies from 2.5GY 8/6 to 2.5GY 7/8. Surface — glabrous.

Fruit:

*Maturity when described.*—Firm ripe.

*Date of first picking.*—Jul. 13, 2011.

*Date of last picking.*—Jul. 20, 2011, varies slightly with climatic conditions.

*Size.*—Medium to large. Average diameter axially 51.0 mm. Average transversely in suture plane 64.3 mm. Average weight 144.8 grams, varies slightly with fertility of the soil, amount of thinning and climatic conditions.

*Form.*—Globose to slightly oblate.

*Suture.*—Nearly smooth, extends from base to apex.

*Ventral surface.*—Nearly smooth.

*Apex.*—Slightly retuse.

*Base.*—Slightly retuse.

*Stem cavity.*—Rounded to slightly elongated in the suture plane. Average depth 5.8 mm. Average diameter 8.4 mm.

Stem:

*Size.*—Small to medium. Average length 15.1 mm. Average diameter 1.6 mm.

*Color.*—Varies from 2.5Y 7/6 to 5YR 5/6.

Flesh:

*Ripens.*—Evenly.

*Texture.*—Firm, meaty.

*Fibers.*—Few, small, tender.

*Firmness.*—Firm, comparable to other commercial varieties.

*Aroma.*—Moderate.

*Amydgalin.*—Undetected.

*Eating quality.*—Very good.

*Flavor.*—Very good, good balance between acid and sugar.

*Juice.*—Heavy amount, enhances flavor.

*Brix.*—Average Brix 17.2°, varies slightly with amount of fruit per tree and climatic conditions.

*Color.*—Varies from 2.5R 3/10 to 2.5R 3/8.

*Pit cavity.*—Average length 22.0 mm. Average width 16.2 mm. Average depth 6.4 mm. Color varies from 2.5R 2/2 to 5R 2/6.

Skin:

*Thickness.*—Medium.

*Surface.*—Smooth.

*Bloom.*—Moderate amount.

*Tendency to crack.*—None.

*Color.*—Ground color varies from 10YR 8/4 to 2.5Y 8/4. Overspread with 5R 2/2 to 2.5R 2/2.

*Tenacity.*—Tenacious to the flesh.

*Astringency.*—Undetected.

Stone:

*Type.*—Clingstone.

*Size.*—Medium. Average length 21.3 mm. Average width 15.9 mm. Average thickness 11.4 mm.

*Form.*—Obovoid.

*Base.*—Flat.

*Apex.*—Acuminate. Average length 1.1 mm.

*Surface.*—Very slightly pitted throughout. One shallow groove on each side of suture extending form base to apex.

*Sides.*—Unequal, one side extending further outward from the suture plane.

*Ridges.*—Very small, extending from base to apex.

*Tendency to split.*—None.

*Color.*—Varies from 5R 3/8 to 2.5R 2/6 when dry.

Kernel:

*Size.*—Small to medium. Average length 13.2 mm. Average width 10.2 mm. Average depth 5.3 mm.

*Form.*—Obovoid.

*Viability.*—Viable, complete embryo development.

*Skin color.*—Varies from 5Y 8.5/8 to 2.5Y 8.5/6.

Use:

*Dessert.*—Market — local and long distance.

Keeping quality: Good, held firm in cold storage at 38-42° F. for 3 weeks without internal breakdown of flesh or appreciable loss of flavor.

Shipping quality: Good, showed minimal skin scarring or flesh bruising of fruit in picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

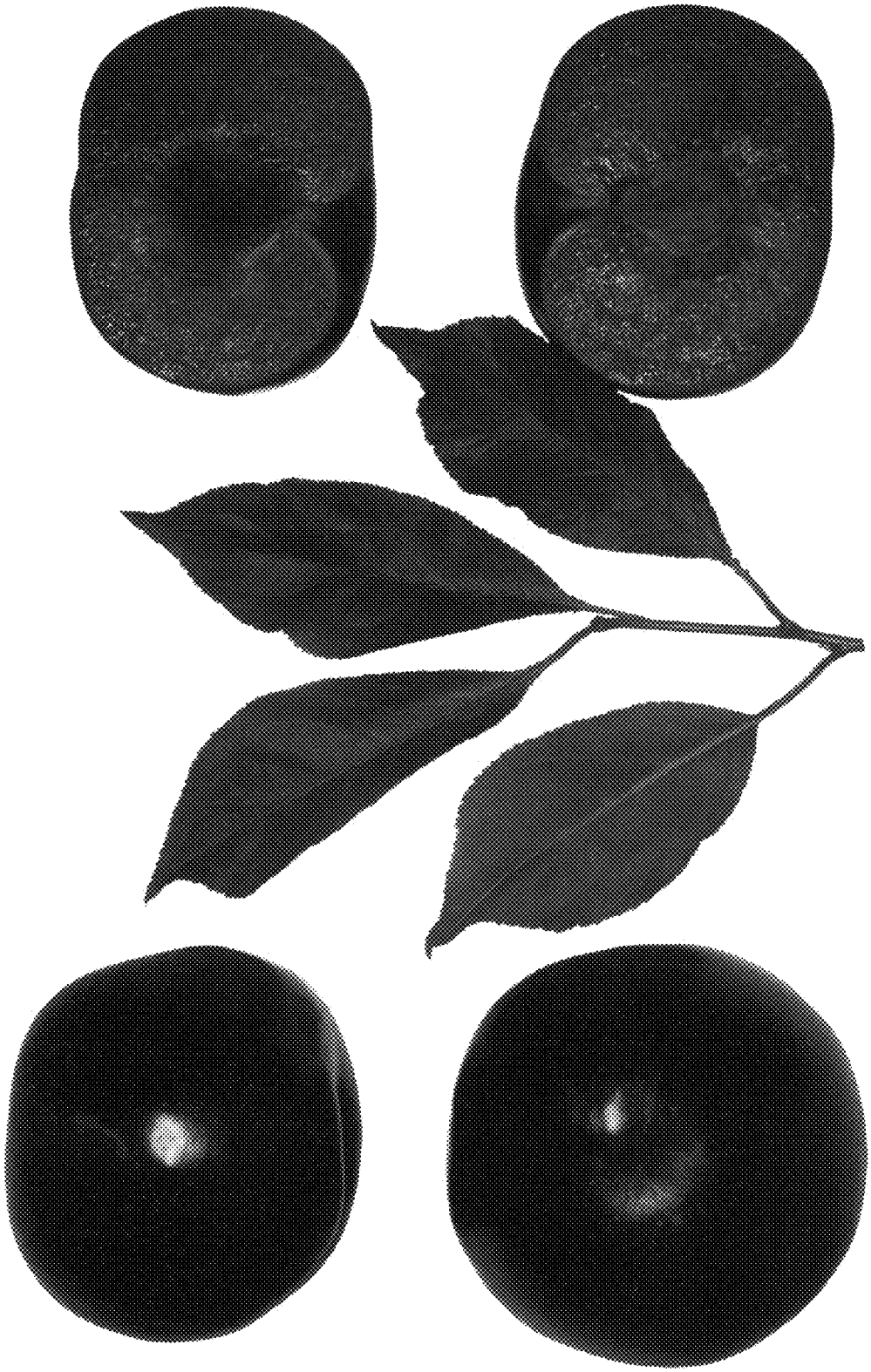

* * * * *